(12) United States Patent
Ward et al.

(10) Patent No.: US 12,272,444 B2
(45) Date of Patent: Apr. 8, 2025

(54) COMPUTER VISION TECHNOLOGIES FOR RAPID DETECTION

(71) Applicant: THE REGENTS OF THE UNIVERSITY OF MICHIGAN, Ann Arbor, MI (US)

(72) Inventors: Kevin Ward, Glen Allen, VA (US); Daniel Francis Taylor, Belleville, MI (US); Michael W Sjoding, Ann Arbor, MI (US); Christopher Elliot Gillies, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 18/180,119

(22) Filed: Mar. 7, 2023

(65) Prior Publication Data
US 2023/0230680 A1    Jul. 20, 2023

Related U.S. Application Data

(63) Continuation of application No. 17/082,145, filed on Oct. 28, 2020, now Pat. No. 11,651,850.
(Continued)

(51) Int. Cl.
*G16H 30/40*    (2018.01)
*G06F 17/18*    (2006.01)
(Continued)

(52) U.S. Cl.
CPC ............. *G16H 30/40* (2018.01); *G06F 17/18* (2013.01); *G06T 7/0012* (2013.01); *G06T 11/20* (2013.01);
(Continued)

(58) Field of Classification Search
CPC .............. G06T 7/0012; G06T 11/20; G06T 2207/10116; G06T 2207/20081;
(Continued)

(56) References Cited

U.S. PATENT DOCUMENTS 9,589,374 B1    3/2017  Gao et al.
10,290,101 B1   5/2019  Podilchuk et al.
(Continued)

FOREIGN PATENT DOCUMENTS

WO   WO-2019217701 A1 * 11/2019   ........... G06F 3/0482
WO   WO-2019245597 A1 * 12/2019   ........... G06F 18/213
WO   WO-2020157761 A1 *  8/2020

OTHER PUBLICATIONS

Benenson, Rodrigo, Stefan Popov, and Vittorio Ferrari. "Large-scale interactive object segmentation with human annotators." Proceedings of the IEEE/CVF conference on computer vision and pattern recognition. 2019.*
(Continued)

*Primary Examiner* — Shefali D Goradia
(74) *Attorney, Agent, or Firm* — MARSHALL, GERSTEIN & BORUN LLP

(57) ABSTRACT

A computing system includes a processor; and a memory having stored thereon an adjustment application comprising computer-executable instructions that, when executed, cause the computing system to: display a graphical user interface including a digital medical image of a patient; superimpose a bounding box; receive an adjustment of an area of interest; and provide an adjusted digital medical image. A non-transitory computer-readable medium includes computer-executable instructions that, when executed via one or more processors, cause a computer to: display a graphical user interface including a digital medical image of a patient; superimpose a bounding box; receive an adjustment of an area of interest; and provide an adjusted digital medical
(Continued)

image. A computer-implemented method includes: displaying a graphical user interface including a digital medical image of a patient; superimposing a bounding box; receiving an adjustment of an area of interest; and providing an adjusted digital medical image.

24 Claims, 6 Drawing Sheets

Related U.S. Application Data

(60) Provisional application No. 62/951,695, filed on Dec. 20, 2019.

(51) Int. Cl.
```
G06T 7/00      (2017.01)
G06T 11/20     (2006.01)
G06V 10/25     (2022.01)
G06V 10/44     (2022.01)
G06V 10/778    (2022.01)
G06V 10/82     (2022.01)
G16H 10/60     (2018.01)
G06V 10/24     (2022.01)
G06V 10/98     (2022.01)
```

(52) U.S. Cl.
CPC ............ *G06V 10/25* (2022.01); *G06V 10/454* (2022.01); *G06V 10/7784* (2022.01); *G06V 10/82* (2022.01); *G16H 10/60* (2018.01); *G06T 2207/10116* (2013.01); *G06T 2207/20081* (2013.01); *G06T 2207/20084* (2013.01); *G06T 2207/30061* (2013.01); *G06T 2210/12* (2013.01); *G06V 10/248* (2022.01); *G06V 10/987* (2022.01)

(58) Field of Classification Search
CPC . G06T 2207/20084; G06T 2207/30061; G06T 2210/12; G16H 10/60; G06F 17/18
See application file for complete search history.

(56) References Cited

U.S. PATENT DOCUMENTS

| | | | |
|---|---|---|---|
| 11,176,415 B2* | 11/2021 | Irshad | G06F 18/41 |
| 2018/0310828 A1 | 11/2018 | DiMaio et al. | |
| 2019/0156484 A1 | 5/2019 | Nye et al. | |
| 2019/0164285 A1 | 5/2019 | Nye et al. | |
| 2020/0098154 A1* | 3/2020 | Marinier | G06F 3/0486 |
| 2020/0161005 A1 | 5/2020 | Lyman et al. | |
| 2020/0211695 A1 | 7/2020 | Zheng et al. | |
| 2021/0366110 A1* | 11/2021 | Oosake | A61B 1/00009 |

OTHER PUBLICATIONS

Wang, Guotai, et al. "Interactive medical image segmentation using deep learning with image-specific fine tuning." IEEE transactions on medical imaging 37.7 (2018): 1562-1573.*

Khaizi, Aida Syafiqah Ahmad, et al. "A mini review on the design of interactive tool for medical image segmentation." 2017 International Conference on Engineering Technology and Technopreneurship (ICE2T). IEEE, 2017.*

Tan, Yanhao, Ke Lu, and Jian Xue. "An Automated Lung Nodule Segmentation Method Based On Nodule Detection Network and Region Growing." Proceedings of the 1st ACM International Conference on Multimedia in Asia. 2019.*

"What is CheXpert?" (2019). Retrieved from the Internet at: <URL:https://stanfordmlgroup.github.io/competitions/chexpert/>.

Bellani et al., "Epidemiology, patterns of care, and mortality for patients with acute respiratory distress syndrome in intensive care units in 50 countries," Jama, 315(8):788-800 (2016).

Ronneberger et al., "U-net: Convolutional networks for biomedical image segmentation." International Conference on Medical image computing and computer-assisted intervention. Springer, Cham, 2015.

Selvaraju et al., "Grad-cam: Visual explanations from deep networks via gradient-based localization," Proceedings of the IEEE International Conference on Computer Vision. 2017.

Zompatori et al., "Overview of current lung imaging in acute respiratory distress syndrome," Eur Respiratory Soc. (2014).

Leiner, T., Rueckert, D., Suinesiaputra, A. et al. Machine learning in cardiovascular magnetic resonance: basic concepts and applications. J Cardiovasc Magn Reson 21, 61 (2019).

U.S. Appl. No. 17/082,145, entitled Computer Vision Technologies for Rapid Detection, filed Oct. 28, 2020.

* cited by examiner

COMPUTER VISION TECHNOLOGIES FOR RAPID DETECTION

CROSS-REFERENCE TO RELATED APPLICATION

This application is a continuation of U.S. patent application Ser. No. 17/082,145, entitled COMPUTER VISION TECHNOLOGIES FOR RAPID DETECTION, filed on Oct. 28, 2020, which claims priority to U.S. Provisional Application No. 62/951,695, entitled COMPUTER VISION TECHNOLOGIES FOR RAPID DETECTION, filed Dec. 20, 2019. The foregoing are incorporated by reference herein in their respective entireties.

STATEMENT OF GOVERNMENTAL INTEREST

This invention was made with government support under HL136687 awarded by the National Institutes of Health and under W81XWH-20-1-0496 awarded by the U.S. Army Medical Research and Materiel Command. The government has certain rights in the invention.

FIELD OF THE DISCLOSURE

The present disclosure is generally directed to methods and systems for rapidly detecting diseases, and more specifically, for training and operating one or more computer vision and machine learning models to analyze image data to facilitate the detection of Acute Respiratory Distress Syndrome (ARDS) and other conditions.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Existing techniques fail to reliably rapidly detect diseases at an early clinical stage. For example, Acute Respiratory Distress Syndrome (ARDS) is a critical illness syndrome that develops in patients with trauma, sepsis, pneumonia and/or aspiration. ARDS is a rapidly progressive disease that causes fluid to leak into the lungs, making breathing difficult or impossible. As such, failing to diagnose ARDS can lead to death or serious illness.

ARDS has a 35% mortality rate. According to the latest definition of ARDS, the diagnosis is based on the onset of hypoxemia and bilateral chest opacities within 1 week of a known risk factor. The presence of bilateral opacities remains one of the hallmarks for diagnosis from a radiological point of view. Therefore, accurate interpretation of a patient's chest x-ray may be a critical component of ARDS detection, and a key driver of the low reliability of ARDS diagnosis. Unfortunately, recognizing ARDS by manually reviewing medical imaging data (e.g., X-ray imaging) is a difficult task even for the skilled, experienced clinician, and ARDS is often misdiagnosed in a hospital setting. The task of recognition is difficult and nuanced for several reasons.

First, rural and/or forward medical locations often lack the equipment necessary to obtain imaging of the resolution/quality necessary for the clinician to form a correct diagnosis. Multiple studies demonstrate that up to 65% of patients with ARDS are diagnosed late or missed, and do not receive evidence-based therapies that improve outcomes. Patients can rapidly develop ARDS in the initial echelons of care including community hospitals, where there may be limited resources and limited access to medical staff with advanced training.

Second, false positives and false negatives are very common due to comorbidities that cause similar symptoms and may include similar imaging results, including an overweight/obese patient, heart failure, Atelectasis (under-inflation of the lung), and collapsed lung. These conditions are often misdiagnosed as ARDS, even in the best of circumstances due to the nuanced, careful interpretation required even by a trained pulmonary specialist to correctly diagnose ARDS. As such, large hospitals often receive patients from smaller hospitals who are said smaller hospital/clinic to have ARDS. Upon examination and imaging, the patients are found to be suffering from a comorbid condition (e.g., heart failure). In such cases, correcting the diagnosis allows for different treatments that cause the patient to improve immediately. Pneumothorax is another condition that is often misdiagnosed and/or missed.

It should be appreciated that the treatment for the comorbidities mentioned above are categorically different than those for treating ARDS, and great harm may come to a patient misdiagnosed with ARDS. For example, Atelectasis is treatable with a simple bedside procedure, and such a condition does not require the extensive treatment procedures required of ARDS treatment that may prove harmful to a misdiagnosed patient. Similarly, ARDS is a rapid-onset disease, and failing to correctly diagnose ARDS (i.e., a false negative) in a timely manner may lead to severe harm to the patient.

Given the fundamental importance to distinguish ARDS and related conditions, and given that such distinctions require nuanced interpretation of imaging data, there is a need for more accurate and consistent methods and systems for diagnosing ARDS and other conditions.

However, medical imaging is highly variable. First, images (e.g., X-rays) are generated by multiple different machine manufacturers, and differ accordingly. Second, images are taken by technicians who manually set the pixel (px) height and width of the images. The variability of imaging is a problem that has not been overcome in known techniques. There is a critical need for new technologies to support the diagnosis of ARDS and other ailments.

BRIEF SUMMARY

In one aspect, a computing system for facilitating a clinician adjustment of a digital medical image corresponding to a patient used in conjunction with a machine learning model includes one or more processors; and one or more memories having stored thereon an adjustment application comprising computer-executable instructions that, when executed, cause the computing system to: (i) display, via the one or more processors, a graphical user interface including the digital medical image corresponding to the patient; (ii) superimpose, over the digital medical image corresponding to the patient, a bounding box containing one or more areas of interest; (iii) receive, via the one or more processors, an adjustment of at least one of the bounding box or the one or more areas of interest; and (iv) provide, via the one or more processors, an adjusted digital medical image corresponding to the patient to the machine learning model, the adjusted digital medical image including the adjustment of at least one of the bounding box or the one or more areas of interest.

In another aspect, a non-transitory computer-readable medium includes computer-executable instructions that, when executed via one or more processors, cause a computer to: (i) display, via the one or more processors, a graphical user interface including the digital medical image corresponding to the patient; (ii) superimpose, over the digital medical image corresponding to the patient, a bounding box containing one or more areas of interest; (iii) receive, via the one or more processors, an adjustment of at least one of the bounding box or the one or more areas of interest; and (iv) provide, via the one or more processors, an adjusted digital medical image corresponding to the patient to the machine learning model, the adjusted digital medical image including the adjustment of at least one of the bounding box or the one or more areas of interest.

In yet another aspect, a computer-implemented method for facilitating a clinician adjustment of a digital medical image corresponding to a patient used in conjunction with a machine learning model includes: (i) displaying, via one or more processors, a graphical user interface including the digital medical image corresponding to a patient; (ii) superimposing, over the digital medical image corresponding to the patient, a bounding box containing one or more areas of interest; (iii) receiving, via one or more processors, an adjustment of at least one of the bounding box or the one or more areas of interest; and (iv) providing, via one or more processors, an adjusted digital medical image corresponding to the patient to a machine learning model, the adjusted digital medical image including the adjustment of at least one of the bounding box or the one or more areas of interest.

BRIEF DESCRIPTION OF THE DRAWINGS

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

For a more complete understanding of the disclosure, reference should be made to the following detailed description and accompanying drawing figures, in which like reference numerals identify like elements in the figures, and in which.

Figure 1:
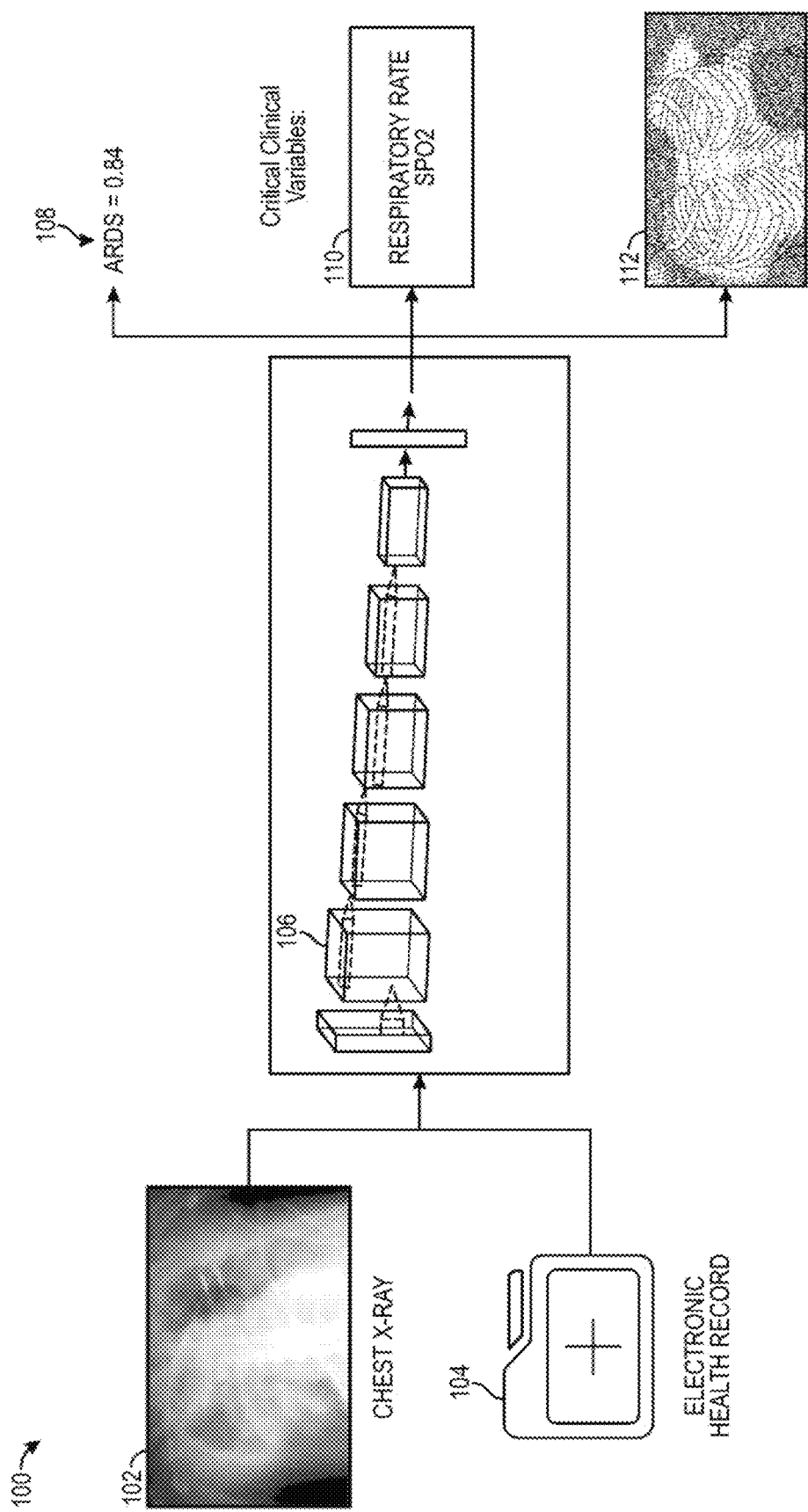
FIG. 1 depicts an exemplary block diagram, according to one embodiment.

The figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

Overview

The embodiments described herein relate to, inter alia, methods and systems for rapidly detecting diseases, and more specifically, for training and operating one or more computer vision and machine learning models to analyze image data to facilitate the detection of Acute Respiratory Distress Syndrome (ARDS) and other conditions.

The present techniques include methods and systems for implementing a decision support system to assist the clinician to identify ARDS true positive diagnoses and avoid false positive diagnoses. For example, the present techniques may process a digital image using one or more machine learning models, to help the clinician to recognize ARDS and institute treatment more quickly. In some embodiments, the present techniques may include identifying true positives of other ailments than ARDS, and therefore assist the clinician to avoid diagnosing false negatives with respect to ARDS.

The present techniques may accept as input a raw chest X-ray for a patient suspected of ARDS, normalize/preprocess the X-ray, and analyze the X-ray using a pre-trained and/or trained deep learning model (e.g., a convolutional neural network (CNN)). The patient's electronic health record (EHR) may be incorporated into the model in some embodiments. For example, the patient's EHR may include data representing a waveform of an electrocardiogram (ECG) of a patient.

The present techniques may output a probability score corresponding to the likelihood of the patient having ARDS, and may highlight key areas of interest within a diagnostic medical image for the radiologist or other clinician to quickly adjudicate the probability score. Similarly, the most important clinical markers (e.g. low oxygenation index) may be supplied to the clinician in embodiments where EHR elements are analyzed. Along with the probability score and clinical markers, the present techniques may overlay the diagnostic image with a heat map showing what areas of the image influenced the model.

In some embodiments, the present techniques may prompt the clinician to recommend that a patient stay in the patient's current location, or move from the patient's location. For example, the physician may recommend that the patient diagnosed by the present techniques as having ARDS be moved from a small hospital or forward operating center to a location with more comprehensive triage facilities to improve the patient's outcome.

As noted above, diagnosing ARDS is nuanced and very difficult, even for highly trained and experienced medical personnel. Currently, clinicians lack modeling tools for diagnosing ARDS. Further, the clinician cannot look into a model and understand how the model is making decision in furtherance of an ultimate clinical judgment based on information that the model is provided with, or to make changes to the model's diagnostic capabilities to improve performance over time. The present techniques address and improve upon each of the limitations in known techniques.

While imaging has long played a key role in the diagnosis and follow-up of ARDS, the present computer vision-based techniques provide expert-level accuracy in the interpretation of medical imaging (e.g., chest x-rays) for the diagnosis of ARDS. Specifically, deep learning methods and systems disclosed herein for detecting ARDS represent a quantum leap for ARDS care and research. Furthermore, the present techniques may be used to provide automated radiologic interpretation deployable to forward operating surgical centers in military applications as well as higher echelons of care, wherein limited computational power has previously limited such applications. The present techniques are particularly beneficial to forward areas on the battlefield and rural community hospitals where resources and access to highly trained personnel and computational resources are limited.

Exemplary Block Diagram

FIG. 1 depicts an exemplary block diagram 100 for rapidly detecting a disease (e.g., Acute Respiratory Distress Syndrome (ARDS)), and more specifically, for training and operating one or more computer vision and machine learning models to analyze image data to facilitate the detection of ARDS and other conditions. The block diagram 100 includes imaging data source 102. In some embodiments, the imaging source 102 is an X-ray machine. The X-ray machine may be used to generate chest X-ray images. The block diagram includes an EHR source 104. The EHR source may be a patient database or another source of suitable patient data.

The imaging data source 102 and the EHR data source 104 may include one or more training data set, and/or one or more diagnostic data set. For example, in an embodiment, the imaging data source 102 may include a large number of images (e.g., 300,000 or more) selected from a publicly-available data set (e.g., the CheXpert dataset). X-rays in dataset may be labeled, and may correspond to an anatomical location (e.g., the chest or thorax). For example, the CheXpert data set is labeled with 14 findings (e.g. consolidation, cardiomegaly, edema, etc.) based on the impression section of the radiology report associated with each image.

The imaging data source 102 data (e.g., a plurality of chest x-rays) may be split at the patient level into multiple groups, each used to train a model to recognize ARDS. For example, the imaging source 102 data may split into a training data set (e.g., comprising 300 patients or more), a validation data set (e.g., comprising 80 patients or more), and a testing set (e.g., comprising 100 patients or more).

In some embodiments, the EHR data source 104 may include EHRs relating to each of the patients. For example, the EHR data source 104 may include laboratory records, past medical history records, physiological variables (e.g., measured oxygenation levels), etc. In some embodiments the EHR data source 104 is not used. However, the EHR data source 104 generally improves the predictions made by the present techniques.

As noted, in addition to training data sets, the imaging data source 102 and EHR data source 104 may provide diagnostic information relating to a patient (i.e., a patient who is undergoing an evaluation). The EHR data source 104 may include one or more medical images of the patient (e.g., one or more chest X-ray, an ECG, etc.) and EHRs, such as a time series of the patient's vitals. Analyzing images from the image data source 102 is sufficient to compute probability of ARDS. However, in some embodiments, using the data available in EHR as additional input to the model assist the model in making more accurate assessments. Further, the EHR data provide help the clinician to index the severity of the patient's condition, and to understand whether patient's health is improving or declining.

It will be appreciated that the machine learning modeling aspects discussed herein may be performed multiple times on multiple sets of images (e.g., sequential X-rays) throughout a patient's stay in the hospital or in another clinical setting. For example, the patient may be imaged once every three hours, or more frequently. Each of the images may be analyzed using the modeling approaches described herein, along with the time series EHR data of the patient's vitals. Analyzing patient vitals and medical imaging data over time in this way provides a much deeper understanding of the patient's condition than does a single snapshot.

The block diagram 100 includes a computer vision system 106 that may analyze the imaging data source 102 data and/or the EHR data source 104 data during a training phase and/or operation phase. For example, the computer vision system 106 may train one or more machine learning model. The machine learning models may include a CNN wherein the CNN comprises multiple sub-networks (e.g., a first sub-network and a second sub-network).

In some embodiments, the present techniques may use transfer learning to pre-train the first sub-network to learn lower-level features (e.g., features related to analyzing radiological images). The present techniques may use the pre-trained first sub-network to train the second sub-network to learn a more specific computer vision analysis task (e.g., to identify ARDS in chest X-ray images). Training and operation of the machine learning techniques are discussed further, below.

The block diagram 100 includes a diagnostic probability score 108, one or more critical clinical markers 110 and a heat map 112 highlighting key areas of interest in the diagnostic images corresponding to patient. In the depicted example, the diagnostic probability score 108 indicates a relatively high probability of ARDS, the clinical markers 110 refer to the patient's respiratory rate and peripheral capillary oxygen saturation (pulse oximetry) as factors indicative of the high probability determination, and the heat map 112 depicts the key areas of interest identified by the machine learning model within the patient's diagnostic image, to assist the diagnostician in quickly adjudicating a final diagnosis. The clinical markers 110 are sourced from the EHR data source 104.

Exemplary Computer-Implemented Method

Medical images are not uniform in orientation or aspect ratio. Therefore, simple resizing of medical images before processing the images using a diagnostic tool (e.g., a machine learning model) may result in inconsistent distortions (e.g., different transformations to the shape of the lungs or heart). Such lack of homogeneity among medical images may further result in sub-optimal performance of the diagnostic tool. To identify areas of interest for a machine learning model (e.g., a machine learning model analyzing the lungs to detect ARDS), the present techniques introduce a series of preprocessing steps that isolate areas of interest (e.g., the lungs) and uniformly transform, or normalize, each image to a predetermined input shape for a machine learning model (e.g., an ARDS classifier).

Figure 2:
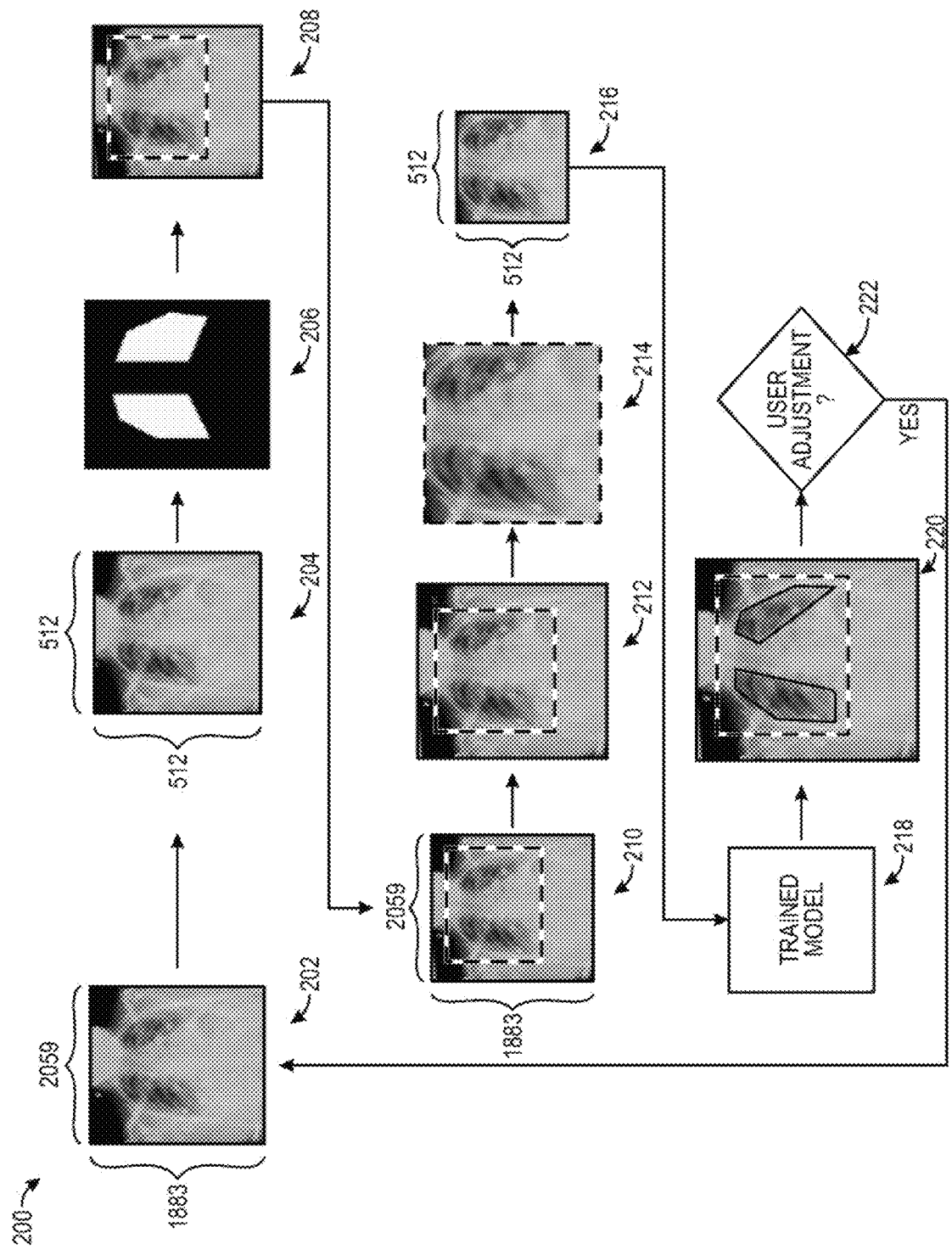
FIG. 2 depicts an exemplary computer-implemented method for rapidly detecting a disease, according to one embodiment and scenario.

FIG. 2 depicts an exemplary graphical method diagram 200 of rapidly diagnosing a disease (e.g., ARDS). The method 200 includes receiving/retrieving an input image (block 202). The input image may be a diagnostic image of a patient, such as an X-ray image captured by a radiological technician, or a training image from a training data set. In general, the dimensions (e.g., height and width) of each X-ray taken in a clinical setting are determined by the radiological technician when the image is taken. For example, the image captured may be an input image of variable dimension (e.g., 1883 h×2059 w). It is of course possible that the image may be a square, however variability may still exist from one technician-produced image to the next.

The method 200 may include reshaping the variable dimension image to a predetermined size, while saving the original aspect ratio of the variable dimension image (block 204). For example, as depicted in FIG. 2, the method 200 may reshape the image into an image of size 512 px×512 px, wherein the respective height and width values of 512 and 512 are predetermined. By way of example, the method 200 may be implemented using any suitable programming languages/techniques (e.g., Python) and the predetermined height and width values may be stored, for example, as hard-coded constants in the implementation code of the programming language, in a database, provided as parameters on the command line, etc. The original aspect ratio may be stored as a value in the memory of a computing system, such as the memory 112 of FIG. 5, the memory 162 of FIG. 5 or the database 180 of FIG. 5. For example, the aspect ratio may be a string value (e.g., "14:3"). Aspect ratio is a distinct value from dimension, yet the two are related. Specifically, by preserving the aspect ratio, the method 200 is able to later perform an inverse transformation of an image while preserving a consistent aspect ratio.

The method 200 may include identifying one or more areas of interest (block 206). In the depicted example, the areas of interest correspond to two lung areas of the patient. In some embodiments, the areas of interest may correspond to other organs/locations (e.g., the heart), or to other anatomical features. In the depicted example, the areas of interest are depicted as geometric shapes in two dimensions. In some embodiments, the areas of interest may be represented as other objects/shapes (e.g., a three-dimensional object). In some embodiments, identifying the one or more areas of interest may include analyzing the medical image using a deep convolutional network (e.g., U-Net). Using a deep convolutional network to identify the one or more areas of interest may advantageously provide superior performance than other methods, while also requiring less training data than other comparable methods. The deep convolutional network used to identify the areas of interest may be trained using chest X-ray images, wherein the lung portions of the X-rays are labeled as such. A user may manually label the images using software that allows the user to draw an image annotation on the training image.

As noted, there is a lack of consistency in medical imaging due to the way that the images are taken. For example, chest X-rays are taken in a hospital in a non-standardized, variable way. The perspective of the chest X-ray may be such that the lung is in one corner of the image or another. Anatomical features other than the heart and lungs may appear in the X-ray. Such variability and noise may cause machine learning models to behave poorly. X-rays are often not square, but images cannot be simply resized without affecting the aspect ratio of the image because, for example, when a machine learning model is attempting to detect enlargement of the heart, affecting the aspect ratio of the image may cause the model to perform poorly.

The present techniques improve the use and application of machine learning models to medical imaging by ensuring that the models are provided with portions of the image that are of interest (e.g., the lung and heart) allowing the model to find those sections to provide the user with the ability to confirm that the model is, in fact, considering the correct portions of the image. The present techniques perform preprocessing and normalization of images to provide this improvement, The method 200 may include identifying a bounding box surrounding the one or more areas of interest (block 208). Identifying the bounding box may be performed by drawing a box, (e.g., a rectangle or square) around the areas of interest identified at block 206.

The method 200 may include mapping the bounding box back to the medical image of received at block 202 (block 210). In some embodiments, mapping the bounding box back to the medical image may include applying an inverse transformation of the reshaping performed at block 204, using the bounding box identified at block 208, while preserving the aspect ratio stored at block 204. The result of this inverse transformation is an image that is identical to the image received at block 202, which additionally includes the bounding box surrounding the areas of interest.

It will be appreciated by those of skill in the art that the mapping of the bounding box to the original image may be performed using suitable graphics processing capabilities. For example, the method 200 may modify the original medical image to include a layer, in some embodiments, and may flatten the layer down on the original image. In some embodiments, the method 200 may generate a copy of the original image including the layer. In still further embodiments, the method 200 may store the original image layer and the bounding box layer in a file format that keeps the layers separated on disk. Advantages to keeping the original medical image is preserving the data in its original state and avoiding any risk of corrupting the file. Advantages to modifying the original image include a more storage-efficient method.

The method 200 may include squaring the medical image including the bounding box, wherein squaring image includes identifying a square crop of the medical image including the bounding box (block 212). Identifying the square image may include identifying a minimum square crop of the image that includes the bounding box. Identifying the minimum square crop may include cropping the original image and/or generating a copy of the original image.

The method 200 may include extracting, from the minimum square image, an image of a sub-area of interest (block 214). In the depicted example of FIG. 2, the image of the sub-area of interest may include the portion of the squared medical image that is within the bounding box. The image of the sub-area of interest may be stored in memory, or as an image file on disk. In some embodiments, the image of the sub-area of interest may be stored as a reference to a crop of the medical image (e.g., using pixel coordinates of the sub-area of interest relative to the medical image). In this way, any crops, aspect ratio information, bounding box data, etc. generated or identified at block 202-212 may be discarded once the sub-area of interest is identified. Discarding such intermediate data advantageously reduces physical storage requirements for the computing system implementing the method 200. Keeping the intermediate information generated/identified may advantageously assist a user in debugging the method 200 and/or in understanding how the image processing pipeline is behaving.

The method 200 may include reshaping the dimensions of the image of the sub-area of interest to a predetermined dimension (e.g., 512 px×512 px) that is suitable for a machine learning model (block 216). By reshaping the image dimensions, the method 200 ensures that the machine learning model will analyze images of uniform shapes.

The method 200 may include analyzing the image of the sub-area of interest using one or more pre-trained/trained machine learning model (block 218). The machine learning models and training/pre-training are discussed in greater detail, below. For example, analyzing the image of the sub-area of interest may include writing the image of the sub-area of interest to a file, a database or a location in computer memory. Another process (e.g., a machine learning model pipeline) may then asynchronously retrieve and process the image of the sub-area of interest. In some embodiments, the method 200 may load the machine learning model into memory, initialize the machine learning model, and pass the image of the sub-area of interest to the initialized model. The method 200 may further receive the result/output of the analysis/execution of the image of the sub-area of interest by the machine learning model and store the output in a suitable location. The method 200 may store the output in association with the medical image, and/or any of the other information generated at the steps 204-216 (e.g., using foreign keys in a relational database, in a directory structure, etc.).

As noted above, the output of the one or more machine learning models may include one or more clinical markers, a heat map highlighting key areas of interest in the medical image, and a diagnostic probability score indicating a probability of ARDS. The method 200 may display this model output and/or the medical image wherein the medical image includes one or both of (a) outlines of the areas of interest identified at block 206, and (b) the bounding box identified at block 208 (block 220). Thus, for example, the method 200 may display to the user, via a display device of a computing device (e.g., a touch screen or other display), the medical image annotated with the outlined areas of concern and/or the bounding box, a probability score determined by the trained machine learning models indicating whether the patient corresponding to the medical image has ARDS, a list of textual clinical markers identified by the machine learning models analyzing the EHR data of the patient as indicative of the model's conclusions with respect to the ARDS diagnosis (or lack thereof), and/or a heat map corresponding to the medical image wherein the areas of concern are highlighted for the physician.

As noted above, the presentation in a computing device of this rich set of information assists the diagnostician in quickly adjudicating a final diagnosis, and is a dramatic improvement over any currently known ad hoc methodologies. Recognizing this, the method 200 includes determining whether the user desires to adjust the bounding box and/or the areas of interest. Specifically, the method 200 includes receiving user input corresponding to an adjustment of the bounding box and/or an adjustment of the areas of interest (block 222). As discussed below, the method 200 may display information to the user, and/or receive input from the user using a suitable computing device. Displaying the rich diagnostic information at block 222 advantageously allows the user to determine whether the system correctly identified the areas of interest and to quickly gauge whether the diagnosis is likely correct or incorrect.

In some embodiments, the user may adjust the bounding box and/or areas of interest, and cause the method 200 to reprocess the image (returning to block 202). When the user causes the reprocessing to occur, the method 200 may track the adjustments made by the user to the bounding box and/or areas of interest (e.g., a repositioning of either within the image) and uses the adjustments as training data for incrementally improving the method 200 over time, or during operation of the deep learning model. For example, in an embodiment, the adjustments provided by the user may be used to relabel and retrain a model using the adjusted image as training data. In another embodiment, the adjustment procedure may be used to improve a deep learning model's first prediction, such that the deep learning model's second prediction takes into account the adjusted positioning of the bounding box and/or the areas of interest in the preprocessing pipeline.

Figure 3A:
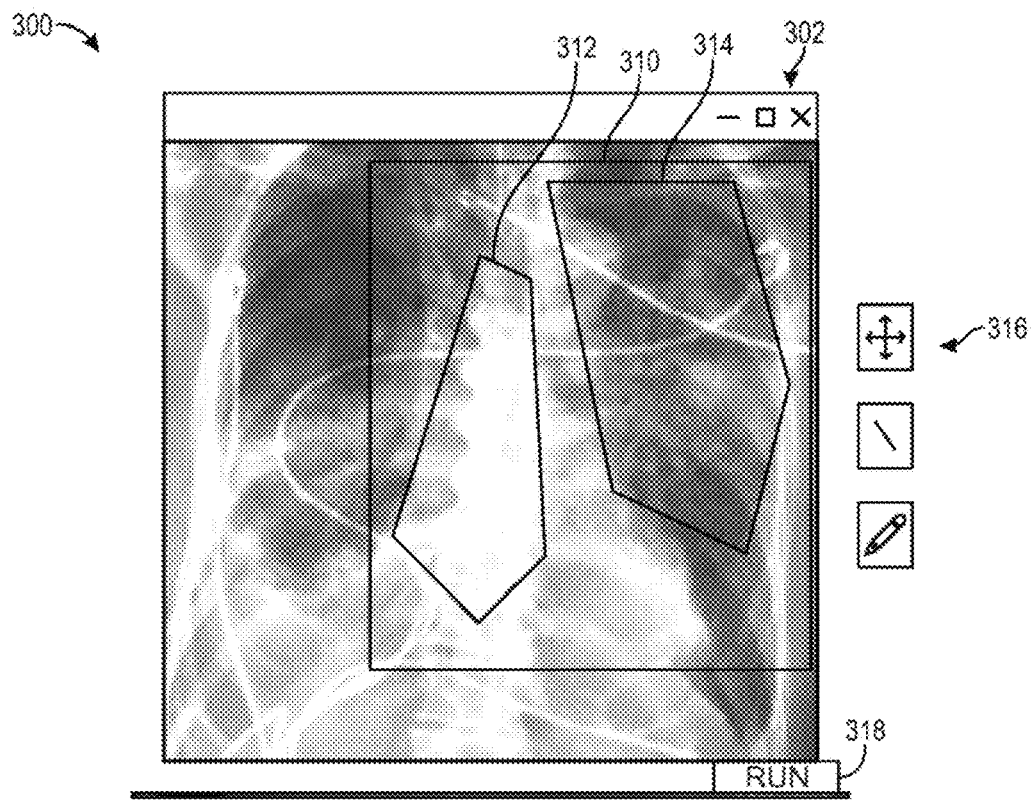
FIG. 3A depicts an exemplary environment for facilitating adjustment to the inputs used in the operation and/or training of the deep learning models described herein.
Figure 3B:
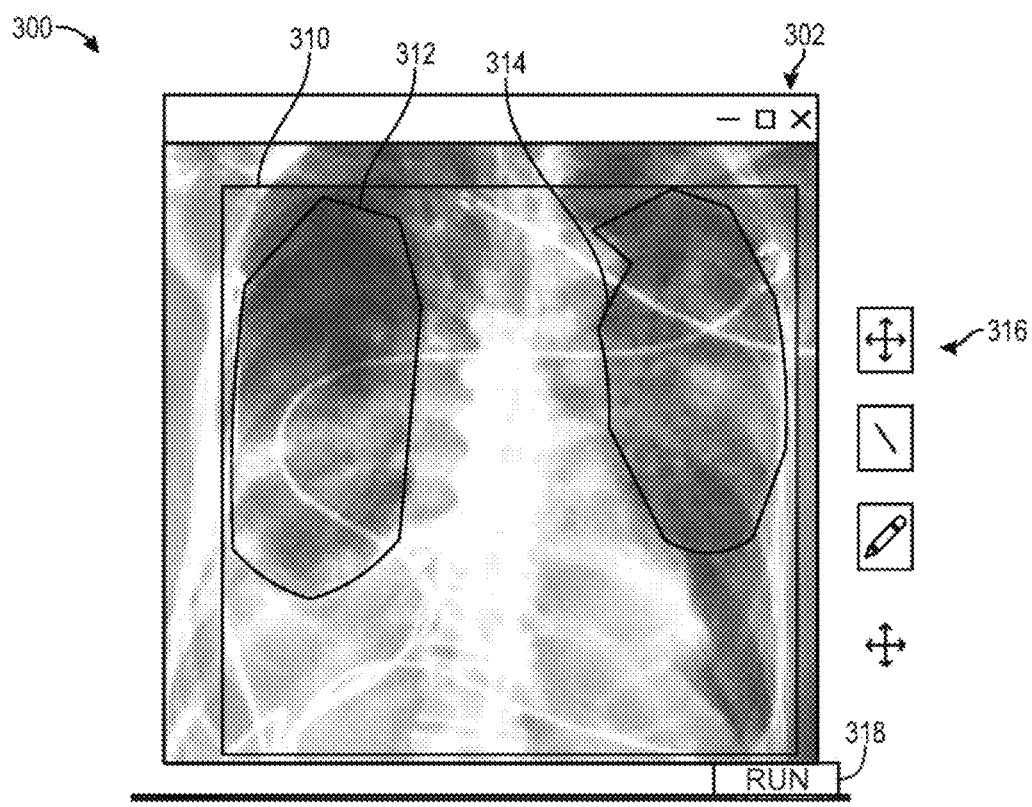
FIG. 3B depicts exemplary adjustments of a user within the environment of FIG. 3A.

Therefore, the more that the user uses the deep convolutional network, the more the network improves over time. Providing the clinician with the ability to modify the model in a feedback loop is highly advantageous, as clinicians are able to understand how the model is making decisions in furtherance of an ultimate clinical judgment based on information provided to the model. FIGS. 3A and 3B depict exemplary user interfaces allowing the clinician to adjust the bounding box and/or areas of interest, and to initiate reprocessing/retraining.

In some embodiments, the blocks 202-216 of the method 200 may be referred to as an image pipeline and may be used for segmenting out the area(s) of interest in a medical image in preparation for processing of that image by a number of different diagnostic tools. The image pipeline may be executed, in some embodiments, in a remote computing device, a cloud computing device, etc. and may receive inputs from and transmit outputs to a "thin" client (i.e., a client computing device having less computational power). Such logical separation of the image pipeline from other system components advantageously uses computational capabilities of distributed computing and parallel computing to more efficiently process large numbers of images.

Exemplary Graphical User Interfaces

FIG. 3A depicts an exemplary environment 300 for facilitating adjustment to the inputs used in the operation and training of the deep learning models described herein. The environment 300 includes an adjustment application 302 that includes a chest X-ray display portion, over which are imposed a bounding box 310, a first area of interest 312 and a second area of interest 314. The bounding box 310 may correspond to the bounding box identified in block 208 of the method 200, for example. The first area of interest 312 and/or second area of interest 314 may each correspond to a respective one of the areas of interest identified at step 206 of the method 200, for example. The adjustment application 302 includes graphical elements 316 that allow the user to adjust (e.g., reposition, rotate, extend, erase, redraw, etc.) one or more of the bounding box 310, the first area of interest 312 and the second area of interest 314. For example, the user may independently reposition any of the bounding box 310, the first area of interest 312 and the second area of interest 314 within the application 302, as shown in FIG. 3B. FIG. 3A includes a user selection element 318 that the user may select to cause a computing system to process an adjusted image.

In operation, the adjustment application 302 may be displayed in a display screen of a computing device of a user (e.g., the client computing device 502 depicted in FIG. 5) during the execution of the method 200 of FIG. 2. For example, the user may input adjustment commands via an input device (e.g., the input device 540 of FIG. 5) to cause the adjustment application 302 to analyze a diagnostic medical image corresponding to a patient.

The adjustment application 302 may be used during pre-training/training and/or operation of the deep learning model. For example, when the model is being trained, the user may use the adjustment application 302 to facilitate providing the model with more accurate, user-refined training examples. In particular, the method 200 may include injecting training images that have passed through the image processing pipeline into the adjustment application 302, and reprocessing any adjustments with respect to those particular training images prior to supplying the images to the model for training.

When the deep learning model is being operated, the user may use the adjustment application 302 to adjust the bounding box and/or areas of interest identified in the image processing pipeline. Once the user has adjusted the bounding box and/or areas of interest, the adjusted information may be passed to the trained deep learning model. Because the deep learning model receives the user's refinements, the deep learning model is likely to make a more accurate prediction. In still further embodiments, the user's adjustments are used both to improve learning and as input to the trained model.

FIG. 3B depicts exemplary user adjustments within the environment 300 of FIG. 3A. Specifically, the user has enlarged the bounding box 310 and reshaped/redrawn the first area of interest 312 and the second area of interest 314.

FIG. 3A depicts an exemplary GUI 400 depicting a medical image 402 that may correspond, for example, to a diagnostic image received from the imaging data source 102 of FIG. 1, the input image received at block 202 of the method 200 of FIG. 2. The image 402 may be generated, for example, by the medical imaging device 508 of FIG. 5. The medical image 402 depicts a patient's chest. The GUI 300 includes an heat map image 404, wherein a heat map layer generated by a deep learning model has been laid over the medical image 402. The heat map image 404 represents regions of concern in the medical image 402 using patterns and/or color, in some embodiments.

As noted above, aspects of the present techniques may overlay the diagnostic images with a heat map showing which areas of the image influenced the model. Specifically, the heat map image 404 may be generated by using a Gradient-weighted Class Activation Mapping (Grad-CAM) algorithm to visualize areas of interest within the medical image 402 that relate to ARDS. Grad-CAM produces a localization map that highlights important regions in the image predicting a certain class (e.g., ARDS=YES or ARDS=NO). The shading and patterns of the heat map image 404 may be depicted in color, in some embodiments, to depict one or more areas where significant opacities in the lungs necessary for the diagnosis of ARDS appear.

Figure 4A:
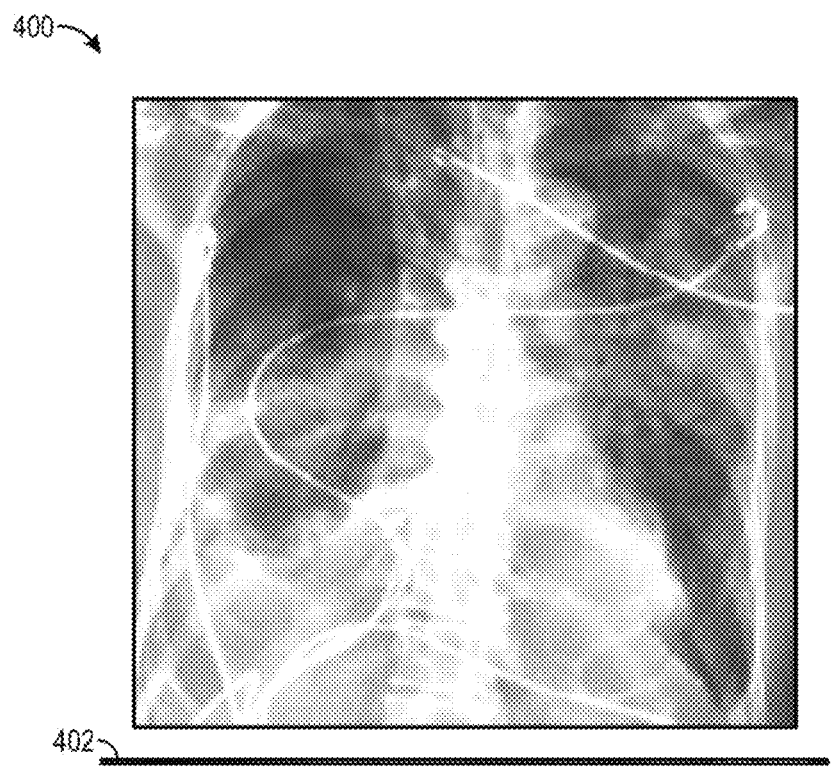
FIG. 4A depicts an exemplary graphical user interface including a class-activation map corresponding to an input image, according to an embodiment.
Figure 4A:
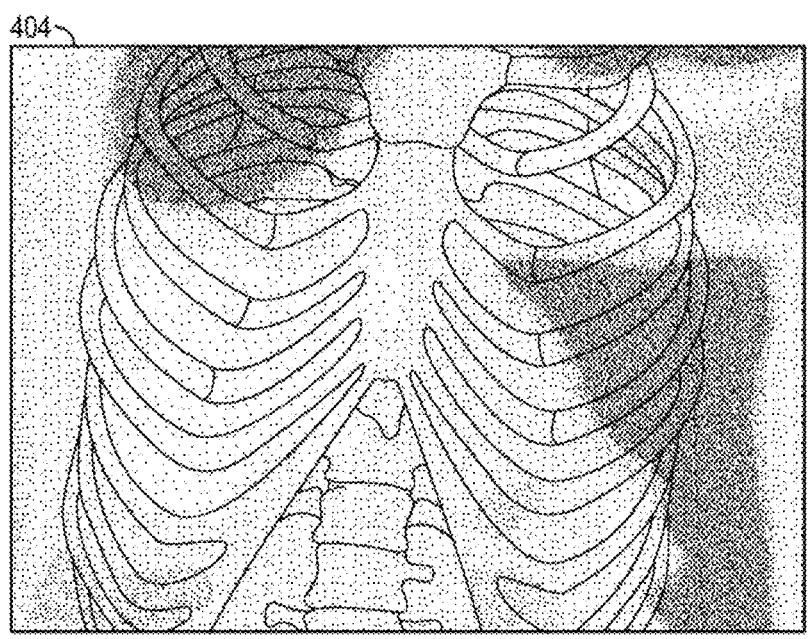
Figure 4B:
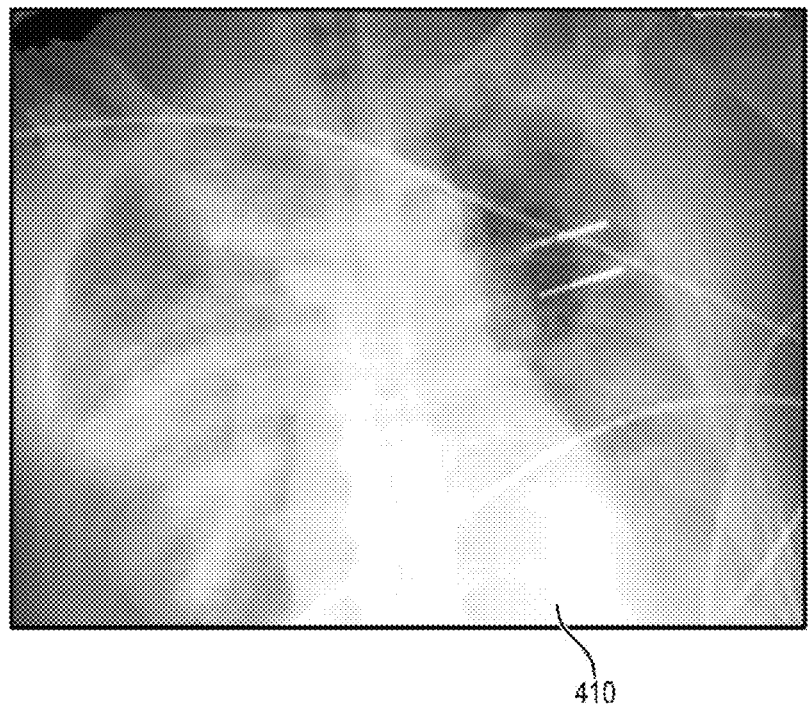
FIG. 4B depicts an exemplary graphical user interface including a class-activation map corresponding to an input image, according to an embodiment.
Figure 4B:
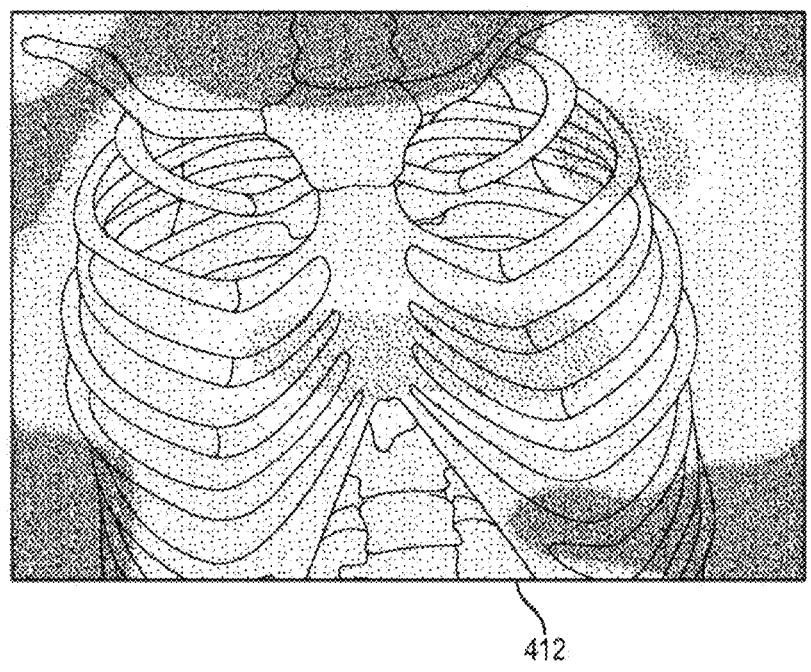

FIG. 4B depicts the exemplary GUI 400 of FIG. 4A in which a second medical image 410 and a heat map image 412 are depicted. FIG. 4B depicts that the deep learning model has learned the importance of opacity in the medical image 412, a defining characteristic in ARDS diagnosis. It should be appreciated that performing the imaging techniques described with respect to FIG. 4A and FIG. 4B to analyze many different types of images is envisioned, including to facilitate clinician review of diseases that relate to the pulmonary organ system and other organ systems.

Exemplary Deep Learning Computing Environment

Figure 5:
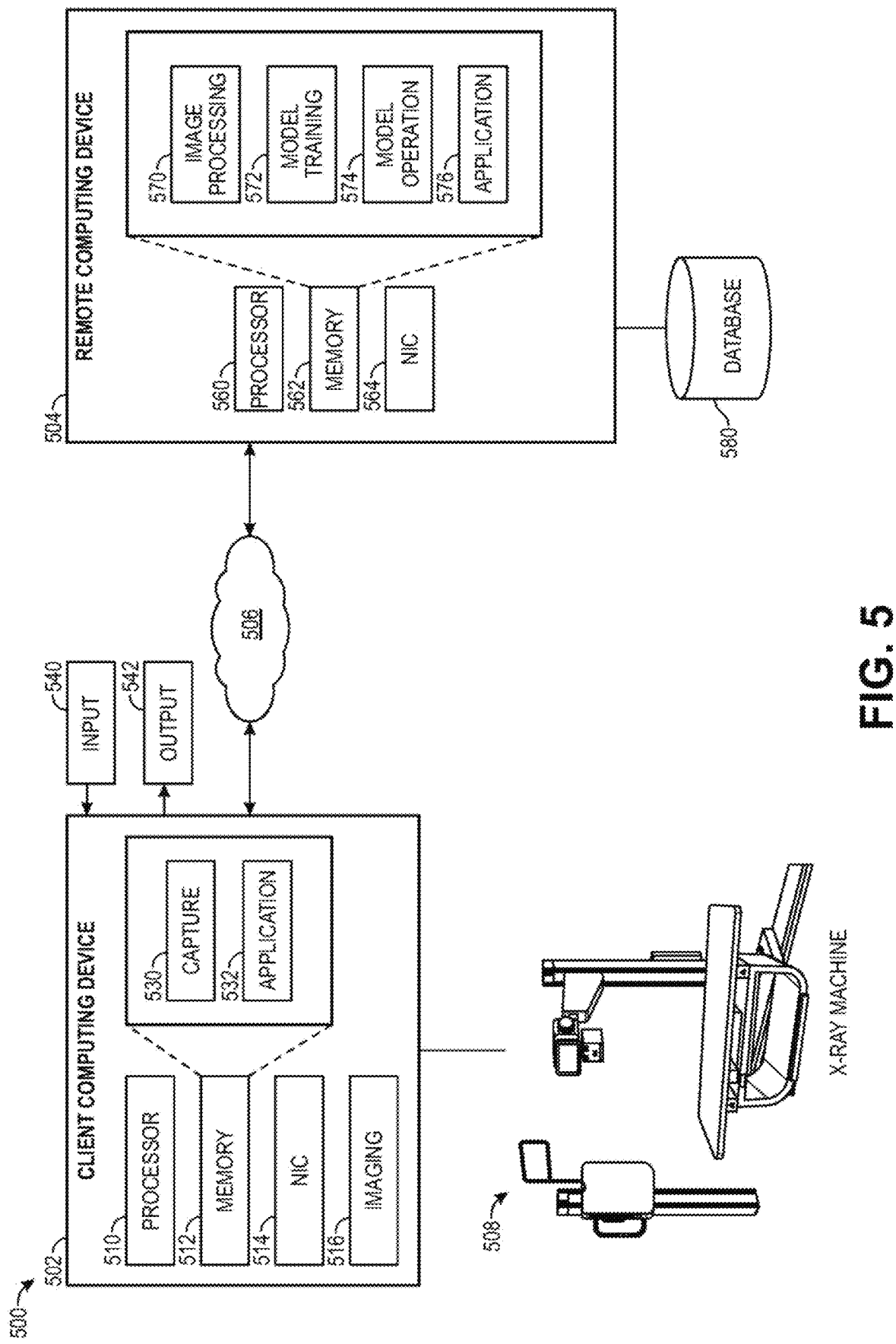
FIG. 5 depicts an exemplary deep learning computing environment for implementing the methods and systems described herein, according to one embodiment and scenario.

FIG. 5 depicts an exemplary deep learning computing environment 500 in which the techniques disclosed herein may be implemented, according to an embodiment.

The environment 500 includes a client computing device 502, a remote computing device 504, a network 506, and a medical imaging device 508. Some embodiments may include a plurality of client computing devices 502, a plurality of remote computing devices 504 and/or a plurality of imaging device 508 that may be configured differently. For example, a first client computing device 502 coupled to the medical imaging device 508 may be used by a radiography technician to capture images of a patient. A second client computing device 502 not coupled to any medical imaging device 508 may be used by a physician to review the results of a machine learning analysis of the captured images or other data. Multiple and/or separate networks may communicatively couple different components, such as the client computing device 502 and the remote computing device 504.

The client computing device 502 may be an individual server, a group (e.g., cluster) of multiple servers, or another suitable type of computing device or system (e.g., a collection of computing resources). For example, the client computing device 502 may be a mobile computing device (e.g., a server, a mobile computing device, a smart phone, a tablet, a laptop, a wearable device, etc.). In some embodiments the client computing device 502 may be a personal computing device of a user (e.g., a radiography technician, a physician, etc.). The client computing device 502 may be communicatively coupled to the remote computing device 504 and/or the medical imaging device 508 via the network 506 or by other means.

The client computing device 502 includes a processor 510, a memory 512 a network interface controller (NIC) 514, and an imaging module 516. The client computing device also include an input device 540 and an output device 542.

The processor 510 may include any suitable number of processors and/or processor types, such as central processing units (CPUs) and one or more graphics processing units (GPUs). Generally, the processor 510 is configured to execute software instructions stored in the memory 512.

The memory 512 may include one or more persistent memories (e.g., a hard drive/solid state memory) and stores one or more set of computer executable instructions/modules, including a capture module 530 and an application module 532, as described in more detail below. More or fewer modules may be included in some embodiments.

The NIC 514 may include any suitable network interface controller(s), such as wired/wireless controllers (e.g., Ethernet controllers), and facilitate bidirectional/multiplexed networking over the network 506 between the client computing device 502 and other components of the environment 500 (e.g., another client computing device 502, the remote computing device 504, etc.).

The imaging module 516 may be located in the memory 512 or in another location of the client computing device 512, and may include a hardware component and/or a software component for communicating with the medical imaging device 508. For example, in some embodiments, the imaging module 516 is a hardware component for communicating with the medical imaging device 508, and a corresponding software component is stored in the memory 512. The imaging module 516 handles the low-level communication required to receive/retrieve medical imaging data from the medical imaging device 508.

The one or more modules stored in the memory 512 may include respective sets of computer-executable instructions implementing specific functionality. For example, in an embodiment, the capture module 530 includes a set of computer-executable instructions for initiating and/or storing a capture (e.g., a file) corresponding to medical image data.

The capture module 530 may include instructions for retrieving/receiving the medical image from the imaging module 516 and encoding the image in a local file or a remote file (e.g., a file in the remote computing device 106). Depending on the embodiment, the capture module 530 may retrieve/receive the medical image data directly from the medical imaging device 508. The capture module 530 may transmit the medical image data in raw form, as an image, etc. via the network 506. Specifically, in some embodiments, the capture module 530 may perform the image capture described with respect to block 202 of FIG. 2.

In some embodiments, the application 532 may display one or more GUIs that allow the user to initiate a capture of an image. For example, the application 132 may analyze input provided by the user to determine one or more event (e.g., a capture event). When the application 532 detects a capture event, the application 532 may initiate a capture of a medical image via the capture module 530. The application 532 allows the user to manage a patient record. For example, the application 532 may include instructions that allow the user to associate medical image data with a user identifier, such as a user name, a medical identification number, an EHR file, etc.

In other embodiments, the application 532 may be an application that is used by a physician to view the results of a machine learning analysis, as depicted in FIG. 3 and FIG. 4. For example, the client computing device 502 may be a tablet and the physician may open the application 532 at the patient's bedside to review the output of the method 200 as described with respect to block 220 of FIG. 2. In some embodiments, the application 532 may also provide GUI screens that allow the user to adjust the areas of interest and/or bounding box, as described with respect to the method 200 at block 222.

The input device 540 may include any suitable device or devices for receiving input, such as one or more microphone, one or more camera, a hardware keyboard, a hardware mouse, a capacitive touch screen, etc. The output device 542 may include any suitable device for conveying output, such as a hardware speaker, a computer monitor, a touch screen, etc. In some cases, the input device 540 and the output device 542 may be integrated into a single device, such as a touch screen device that accepts user input and displays output.

The user may interact with the application 532 via the input device 540 and/or the output device 542. Specifically, the application module 532 may include computer-executable instructions that receive user input via the input device 540 and/or display one or more GUIs on the output device 542. For example, the application module 532 may correspond to a mobile computing application (e.g., an Android, iPhone, or other) computing application. The application 532 may be a specialized application corresponding to the type of computing device embodied by the client computing device 502. For example, in embodiments where the client computing device 502 is a mobile phone, the mobile application module may correspond to a mobile application downloaded for an iPhone. When the client computing device 502 is a tablet, the application module 532 may correspond to an application with tablet-specific features.

In some embodiments, one or more components of the computing device 502 may be embodied by one or more virtual instances (e.g., a cloud-based virtualization service). In such cases, one or more client computing device 502 may be included in a remote data center (e.g., a cloud computing environment, a public cloud, a private cloud, etc.). For example, a remote data storage module (not depicted) may remotely store data received/retrieved by the computing device 502.

The network 506 may include any suitable combination of wired and/or wireless communication networks, such as one or more local area networks (LANs), metropolitan area networks (MANs), and/or wide area network (WANs). As just one specific example, the network 506 may include a cellular network, the Internet, and a server-side LAN. As another example, the network 506 may support a cellular (e.g., 4G) connection to the client computing device 502, and an IEEE 802.11 connection to the remote computing device 504.

The client computing device 502 may be configured to communicate bidirectionally via the network 506 with the remote computing device 504 and/or the medical imaging device 508. For example, the application 532 may transmit captured image data (e.g., X-ray imaging) and/or user requests to the remote computing device 504, and may receive/retrieve information (e.g., machine learning model outputs) from the remote computing device 504.

The medical imaging device 508 may include one or more machine used to perform medical projectional radiography, computed tomography (CT) scanning or magnetic resonance imaging (MRI) scanning. For example, a first medical imaging device 508 may be an X-ray machine for imaging prone patients, and a second medical imaging device may be a second X-ray machine for imaging standing patients.

The remote computing device 504 includes a processor 560, a memory 562, and a NIC 546. The processor 560 may include any suitable number of processors and/or processor types, such as one or more CPUs and/or one or more GPUs. GPUs may be used to drastically accelerate certain operations performed by the remote computing device 504, such as model training. Generally, the processor 560 is configured to execute software instructions stored in the memory 562. The memory 562 may include one or more persistent memories (e.g., a hard drive/solid state memory) and stores one or more set of computer executable instructions/modules, as discussed below. For example, the remote computing device 504 may include an image processing module 570, a model training module 572, a model operation module 574, and an application module 576. More or fewer modules may be included, in some embodiments. The NIC 564 may include any suitable network interface controller(s), such as wired/wireless controllers (e.g., Ethernet controllers), and facilitate bidirectional/multiplexed networking over the network 506 between the remote computing device 504 and other components of the environment 100 (e.g., another remote computing device 504, the client computing device 502, etc.).

The remote computing device 508 may be communicatively coupled to a database 580. The database 580 may be implemented as a relational database management system (RDBMS) in some embodiments. For example, the database 580 may include one or more structured query language (SQL) database, a NoSQL database, a flat file storage system, or any other suitable data storage system/configuration. In general, the database 580 allows the client computing device 502 and/or the remote computing device 504 to create, retrieve, update, and/or retrieve records relating to performance of the techniques herein.

For example, the database 580 allows the components of the environment 500 to store information received from one or more medical imaging devices 508, to access training and pre-training data sets, as discussed below with respect to model training and model operation, and to access EHR data. Specifically, the database may implement the imaging data source 102 and the EHR data source 104 discussed with respect to FIG. 1. In some embodiments, the client computing device 502 may include a module (not depicted) including a set of instructions for querying the database 580. For example, the client computing device 502 may include a set of database drivers for accessing the database 580 of the remote computing device 504. In some embodiments, the database 580 may be located remotely from the remote computing device 54, in which case the remote computing device 504 may access the database 580 via the NIC 564 and the network 506.

The one or more modules stored in the memory 562 include respective sets of computer-executable instructions implementing specific functionality.

For example, the image processing module 570 may include computer-executable instructions for performing image manipulation operations, such as cropping, de-noising, sharpening, masking, manipulating images, accessing metadata, accessing raw pixel values, splitting and merging of images, setting image regions, modifying pixel values, manipulating image layers, etc. In some embodiments, the image processing module 570 may include a software library of image processing functionality, such as OpenCV. In some embodiments, the image processing module 570 may include image processing instructions/libraries specific to accessing specific radiological imaging types (e.g., an X-ray imaging library, a CT-scan imaging library, etc.). The remote computing device 504 may use the image processing module 570 to perform one or more the steps of the method 200. For example, the remote computing device 504 may use the image processing module 570 to crop, square, reshape, overlay boundary layers, etc. The remote computing device 504 may use the image processing module 570 to generate the composite image at block 220 of FIG. 2, and/or to generate heat maps.

The model training module 572 may include computer-executable instructions for training the one or more machine learning models described above. The model training module may incorporate one or more software libraries/frameworks (e.g., Google TensorFlow, Caffe, PyTorch, Keras, etc.) for model training.

In some embodiments, the model training module 572 may use transfer learning techniques in training one or more machine learning models to analyze one or more medical images to predict the probability that the patient corresponding to the medical images has ARDS or another condition. For example, in some embodiments, the model training module 572 may train a deep machine learning model (e.g., a CNN) using transfer learning, wherein the transfer learning comprises a pre-training and a training step.

In some embodiments, the model training module 572 trains a deep learning model having, for example, an n-layer dense network architecture, wherein n is any positive integer (e.g., 121 or more). The model training module 572 may pre-train the deep learning model using an existing data set of medical imaging information (e.g., the CheXpert dataset). The pre-training may include training the deep learning model on many (e.g., 300,000 or more) images that do not include images of the condition that the deep learning model is being trained to detect (e.g., ARDS). As noted above, the training data may be labeled with findings relating to the impression section of the radiology report associated with each image. The model training module 572 may access the training data in the database 580. As noted above, the imaging data used to train the deep learning model may be retrieved/received from an imaging data source, and is split at the patient level into training, validation and testing data sets, each used to train the deep learning model.

Pre-training by the model training module 572 may advantageously allow the deep learning model to learn generalizable representations of medical images (e.g., curves, lines, etc.) that are the building blocks of the medical images. This allows the deep learning model to robustly detect particular conditions, because the deep learning model has learned to identify lower level features extracted from the medical image that are relevant to performing a variety of classification tasks on the image.

In some embodiments, the model training module 572 freezes some or all of the layers of the deep learning model as part of the pre-training. For example, all layers except for the last layer of a CNN comprising the deep learning model and subsequent layers may be frozen. Freezing some portions of the network advantageously decreases training time and reduces the amount of computation necessary to train the deep learning model.

In some embodiments, the model training module 572 may apply some or all of the image processing pipeline steps discussed with respect to FIG. 2 to the training images. For example, prior to pre-training the deep learning module, the model training module 572 may use the image processing module 570 to perform the following operations on one or more training image: reshaping the training image to a predetermined size, while saving the original aspect ratio of the variable dimension training image; identifying one or more areas of interest of the training image; identifying a bounding box surrounding the one or more areas of interest of the training image; mapping the bounding box back to the training image; squaring the training image including the bounding box, wherein squaring the training image includes identifying a square crop of the training image including the bounding box; extracting, from the training image, an image of a sub-area of interest; and reshaping the dimensions of the training image of the sub-area of interest to a predetermined dimension.

The above-noted benefits of the preprocessing and normalizing of the training image includes at least all of the benefits of preprocessing and normalizing the diagnostic images, as well as increasing the overall predictive accuracy of the model.

Once the model training module 572 has pre-trained the deep learning model, the model training module 572 may serialize the deep learning model (including model weights) and store the deep learning model in the memory 562 and/or in the database 580. The deep learning model training module 572 may later deserialize the deep learning model and perform additional training. Other modules may also deserialize (i.e., load) the pre-trained/trained deep learning model, including the model operation module 574.

The model training module 572 may further train the pre-trained deep learning module for the specific task of detecting one or more medical condition. Specifically, in an embodiment, the model training module 572 may further train the unfrozen layers of the deep learning model that remain after freezing the pre-trained model using a data set consisting of a number of images (e.g., 10,000) labeled as ARDS/NOT-ARDS by pulmonary specialist physicians who analyzed respective EHR corresponding to each image during the labeling process.

The model training module 572 may cause the trained model to output single probability score corresponding to the likelihood that an input image provided to the pre-trained and trained model corresponds to a patient who has ARDS, as depicted in the diagnostic probability score 108 of FIG. 1.

Empirical testing has demonstrated that the machine learning approaches described herein have performed as well as, and in some cases better than, skilled human reviewers in the analysis of medical imaging (e.g., X-rays) for detecting certain conditions (e.g., ARDS, congestive heart failure, pneumonia, hemothorax, pneumothorax, atelectasis, pleural effusion, tuberculosis, etc.).

Once the deep learning model is pre-trained and/or trained, the model operation module 574 may operate the deep learning model to analyze a diagnostic image. Specifically, the model operation module 574 may load the trained deep learning model into memory, and operate the deep learning model as described with respect to FIG. 2, above. The model operation module may preprocess the diagnostic image to reshape, square, and normalize the diagnostic image. The model operation module 574 may annotate the diagnostic image with areas of interest and a bounding box.

The model operation module 574 may provide the bounded area of interest to the pre-trained/trained deep learning model to generate a probability score corresponding to the diagnostic probability score 108 of FIG. 1, one or more clinical markers or other EHR information corresponding to the one or more clinical markers 110 of FIG. 1, and one or more heat map corresponding to the one or more heat map 112 of FIG. 1 and/or the heat map 304 of FIG. 3 and the heat map 404 of FIG. 4.

In some embodiments, the model operation module 574 may generate a composite image, such as the composite image depicted in block 220 of FIG. 2, wherein the diagnostic image includes the bounding box and/or areas of interest identified by the deep learning model, applied as layers over the diagnostic image. The composite image may be provided with the probability score, clinical markers, and/or heat map to any component of the environment 500, and each may be processed further.

For example, in some embodiments, the model training module 572 may not include EHR data when training the deep learning model, and may rather train a separate classifier model using the EHR data. In that case, after analyzing the diagnostic image using the trained deep learning model, the operation module 574 may operate the classifier model to obtain a separate EHR data severity score relative to the patient. The severity score may be based on, for example, a time series of one or more of the patient's vitals. In that case, the model operation module 574 may further process the probability score of the deep learning model by factoring the patient severity score into the probability score, to determine a combined risk score. The combined risk score may be representative of the model's confidence that the user has ARDS, based on analyzing the diagnostic image and the EHR data.

As noted, the present techniques may be used in embodiments that do and do not incorporate EHR. However, incorporating EHR may provide better model accuracy and allow experts and non-experts to make better diagnoses. For example, in some embodiments, the model operation module 574 may add a further level of diagnostic information to the ARDS diagnosis. For example, when the deep learning module indicates the presence of ARDS, the model operation module 574 may execute additional instructions that analyze the EHR of the patient to grade the severity of state of patient, including operating one or more modules to predict the trajectory of the disease in the patient. Such predictions may include an expected days on ventilator, a likelihood of mortality, etc.

By analyzing sequential imaging, the present techniques may track patient trajectory. For instance, the physician may quickly determine how quickly a patient is worsening if the probability score increases from 0.4 to 0.6. Preventative measures and monitoring could then be put in place to prevent a more catastrophic event.

The model training module 572 may convert the probability score into a scaled score, or threshold the score to provide a binary diagnostic classification. For example, a probability score greater than 80% may be considered a positive indication of an ARDS diagnosis, while 80% or less may not. In some embodiments, the classifier may be added to the deep learning model by the model training module 572 during the training phase as an additional layer of the deep learning model.

When the trained deep learning model analyzes the diagnostic image, the model operation module 574 may receive the output of the model and store the output (e.g., in the memory 562 and/or the database 580) or transmit the output via the network 506. For example, the model operation module 574 may transmit the output to the client computing device 502 for display to the user by one or more GUIs of the application module 532 via the output device 542.

It should be appreciated that the deep learning model may be trained for additional use cases, beyond ARDS. Specifically, in many patients, a negative diagnosis for ARDS may be understood as a positive diagnosis for another, related condition such as heart failure. For example, the present techniques may allow the user to upload (e.g., via a remote computing device) de-identified images, to determine the presence of ARDS in large patient populations. Similar approaches can be taken with other severe medical conditions where chest imaging interpretation is critical to the diagnosis such as heart failure.

The present techniques provide advantages over known techniques, at least by reducing the number of false positives and false negatives when diagnosing nuanced pulmonary conditions, automatically normalizing images to improve the accuracy of non-uniform real-world imaging data, and grading the severity of the patient who has ARDS. The present techniques allow the clinician to determine that someone has ARDS and stop misdiagnoses early, which is of essential clinical value. The present techniques are of particular importance in rural settings, and forward operating settings where a pulmonologist may not be available. In some cases, the present techniques may be used to rule out ARDS in favor of a less threatening condition prior to transferring a patient, thereby saving substantial resources.

ADDITIONAL CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A computing system for facilitating a clinician adjustment of a digital medical image corresponding to a patient used in conjunction with a machine learning model, comprising:
   one or more processors; and
   one or more memories having stored thereon an adjustment application comprising computer-executable instructions that, when executed, cause the computing system to:
   train, via the one or more processors, the machine learning model to learn to detect acute respiratory distress syndrome based on an opacity of the digital medical image;
   display, via the one or more processors, a graphical user interface including the digital medical image corresponding to the patient;
   superimpose, over the digital medical image corresponding to the patient, a bounding box containing one or more areas of interest;
   receive, via the one or more processors, an adjustment of at least one of the bounding box or the one or more areas of interest; and
   provide, via the one or more processors, an adjusted digital medical image corresponding to the patient to the machine learning model, the adjusted digital medical image including the adjustment of at least one of the bounding box or the one or more areas of interest.

2. The computing system of claim 1, the adjustment application comprising further instructions that, when executed by the one or more processors, cause the computing system to:
   capture, via an imaging device, the digital medical image corresponding to the patient.

3. The computing system of claim 1, wherein the adjustment of at least one of the bounding box or the one or more areas of interest is at least one of a repositioning, a rotation, an extension, an erasure, or a redrawing.

4. The computing system of claim 1,
   wherein the machine learning model is a deep learning model being trained, and
   the adjustment application comprising further instructions that, when executed by the one or more processors, cause the computing system to:
   inject the adjusted digital medical image corresponding to the patient to an image processing pipeline;
   reprocess the adjusted digital medical image; and
   provide the adjusted digital medical image to the deep learning model to facilitate training of the deep learning model.

5. The computing system of claim 1,
   wherein the machine learning model is a trained deep learning model being operated, and
   the adjustment application comprising further instructions that, when executed by the one or more processors, cause the computing system to:
   provide the adjusted digital medical image to the trained deep learning model to improve predictive accuracy of the deep learning model.

6. The computing system of claim 1,
   wherein the digital medical image is a chest X-ray image, and
   wherein the one or more areas of interest include one or more heat maps generated using a Gradient-weighted Class Activation Mapping (Grad-CAM) algorithm.

7. The computing system of claim 1,
   wherein the digital medical image corresponds to a projectional radiography image, computed tomography (CT) scanning image or a magnetic resonance imaging (MRI) scanning image.

8. The computing system of claim 1, wherein the machine learning model is trained to detect at least one of acute respiratory distress syndrome, trauma, sepsis, pneumonia, aspiration, congestive heart failure, hemothorax, pneumothorax, atelectasis, collapsed lung, pleural effusion or tuberculosis.

9. A non-transitory computer-readable medium having stored thereon computer-executable instructions that, when executed via one or more processors, cause a computer to:
   train, via one or more processors, the machine learning model to learn to detect acute respiratory distress syndrome based on an opacity of the digital medical image;
   display, via one or more processors, a graphical user interface including a digital medical image corresponding to a patient;
   superimpose, over the digital medical image corresponding to the patient, a bounding box containing one or more areas of interest;
   receive, via one or more processors, an adjustment of at least one of the bounding box or the one or more areas of interest; and
   provide, via one or more processors, an adjusted digital medical image corresponding to the patient to a machine learning model, the adjusted digital medical image including the adjustment of at least one of the bounding box or the one or more areas of interest.

10. The non-transitory computer-readable medium of claim 9, having stored thereon computer-executable instructions that, when executed via one or more processors, cause a computer to:
    capture, via an imaging device, the digital medical image corresponding to the patient.

11. The non-transitory computer-readable medium of claim 9, wherein the adjustment of at least one of the bounding box or the one or more areas of interest is at least one of a repositioning, a rotation, an extension, an erasure, or a redrawing.

12. The non-transitory computer-readable medium of claim 9,
    wherein the machine learning model is a deep learning model being trained, and
    the computer-readable medium having stored thereon computer-executable instructions that, when executed via one or more processors, cause a computer to:
    inject the adjusted digital medical image corresponding to the patient to an image processing pipeline;
    reprocess the adjusted digital medical image; and
    provide the adjusted digital medical image to the deep learning model to facilitate training of the deep learning model.

13. The non-transitory computer-readable medium of claim 9,
    wherein the machine learning model is a trained deep learning model being operated, and
    the computer-readable medium having stored thereon computer-executable instructions that, when executed via one or more processors, cause a computer to:

provide the adjusted digital medical image to the trained deep learning model to improve predictive accuracy of the deep learning model.

14. The non-transitory computer-readable medium of claim 9,
wherein the digital medical image is a chest X-ray image, and
wherein the one or more areas of interest include one or more heat maps generated using a Gradient-weighted Class Activation Mapping (Grad-CAM) algorithm.

15. The non-transitory computer-readable medium of claim 9, wherein the machine learning model is trained to detect at least one of acute respiratory distress syndrome, trauma, sepsis, pneumonia, aspiration, congestive heart failure, hemothorax, pneumothorax, atelectasis, collapsed lung, pleural effusion or tuberculosis.

16. The non-transitory computer-readable medium of claim 9,
wherein the digital medical image corresponds to a projectional radiography image, computed tomography (CT) scanning image or a magnetic resonance imaging (MRI) scanning image.

17. A computer-implemented method for facilitating a clinician adjustment of a digital medical image corresponding to a patient used in conjunction with a machine learning model, the method comprising:
training, via one or more processors, the machine learning model to learn to detect acute respiratory distress syndrome based on an opacity of the digital medical image;
displaying, via one or more processors, a graphical user interface including the digital medical image corresponding to a patient;
superimposing, over the digital medical image corresponding to the patient, a bounding box containing one or more areas of interest;
receiving, via one or more processors, an adjustment of at least one of the bounding box or the one or more areas of interest; and
providing, via one or more processors, an adjusted digital medical image corresponding to the patient to a machine learning model, the adjusted digital medical image including the adjustment of at least one of the bounding box or the one or more areas of interest.

18. The computer-implemented method of claim 17, further comprising:
capture, via an imaging device, the digital medical image corresponding to the patient.

19. The computer-implemented method of claim 17, wherein the adjustment of at least one of the bounding box or the one or more areas of interest is at least one of a repositioning, a rotation, an extension, an erasure, or a redrawing.

20. The computer-implemented method of claim 17,
wherein the machine learning model is a deep learning model being trained, and
further comprising:
injecting the adjusted digital medical image corresponding to the patient to an image processing pipeline;
reprocessing the adjusted digital medical image; and
providing the adjusted digital medical image to the deep learning model to facilitate training of the deep learning model.

21. The computer-implemented method of claim 17,
wherein the machine learning model is a trained deep learning model being operated, and
further comprising:
providing the adjusted digital medical image to the trained deep learning model to improve predictive accuracy of the deep learning model.

22. The computer-implemented method of claim 17,
wherein the digital medical image is a chest X-ray image, and
wherein the one or more areas of interest include one or more heat maps generated using a Gradient-weighted Class Activation Mapping (Grad-CAM) algorithm.

23. The computer-implemented method of claim 17, wherein the machine learning model is trained to detect at least one of acute respiratory distress syndrome, trauma, sepsis, pneumonia, aspiration, congestive heart failure, hemothorax, pneumothorax, atelectasis, collapsed lung, pleural effusion or tuberculosis.

24. The computer-implemented method of claim 17,
wherein the digital medical image corresponds to a projectional radiography image, computed tomography (CT) scanning image or a magnetic resonance imaging (MRI) scanning image.

* * * * *